United States Patent [19]

Flam et al.

[11] Patent Number: 5,431,152
[45] Date of Patent: Jul. 11, 1995

[54] ORAL FIBEROPTIC INTUBATING APPARATUS AND METHOD

[76] Inventors: Gary H. Flam, 2244 Robinhood, Houston, Tex. 77005; Susan W. Gilbert, 3235 Locke La., Houston, Tex. 77019

[21] Appl. No.: 124,016

[22] Filed: Sep. 21, 1993

[51] Int. Cl.⁶ .................................. A61B 1/26
[52] U.S. Cl. .................. 600/120; 600/182; 600/156
[58] Field of Search ............... 606/108–113, 606/106; 128/10, 11, 6, 4; 604/281

[56] References Cited

U.S. PATENT DOCUMENTS

| | | | |
|---|---|---|---|
| 3,314,431 | 4/1967 | Smith, Jr. | 606/108 X |
| 4,432,350 | 2/1984 | Brieslav et al. | 128/10 |
| 4,437,458 | 3/1984 | Upsher | 128/11 |
| 4,567,882 | 2/1986 | Heller | 128/11 |
| 5,003,963 | 4/1991 | Bullard et al. | 128/11 |
| 5,095,888 | 3/1992 | Hawley | 128/10 |
| 5,203,320 | 4/1993 | Augustine | 128/10 |
| 5,219,345 | 6/1993 | Potter | 606/15 |
| 5,279,281 | 1/1994 | Harvey | 128/11 X |

FOREIGN PATENT DOCUMENTS 107779 5/1984 European Pat. Off. ............ 606/108

Primary Examiner—Peter A. Aschenbrenner
Attorney, Agent, or Firm—Kenneth A. Roddy

[57] ABSTRACT

An endotracheal intubating instrument has an elongate curvilinear blade member releasably attachable to a handle and a central channel sized to removably receive and slidably engage an endotracheal tube therein, an elongate tubular housing removably connected at its forward end to the rearward end of the endotracheal tube which removably receives a fiberoptic scope having an eyepiece at a rearward end and a fiberoptic bundle extending forwardly within the endotracheal tube, and an adjustable positioning element through which the forwardly extending fiberoptic bundle passes for adjustably positioning and maintaining the tip end of the fiberoptic bundle relative to the forward end of the endotracheal tube. The apparatus is placed in the mouth, the larynx is identified, and the endotracheal tube, housing, and fiberoptic scope are advanced as a unit into the trachea as the blade is removed. Then the fiberoptic scope and housing are withdrawn, leaving the endotracheal tube in the desired part of the trachea.

16 Claims, 6 Drawing Sheets

FIG. 6
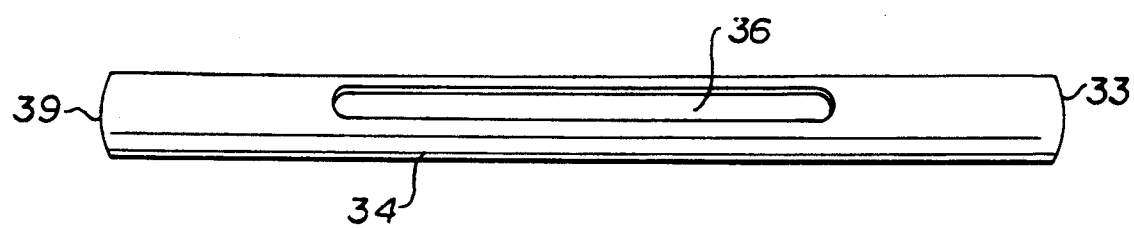
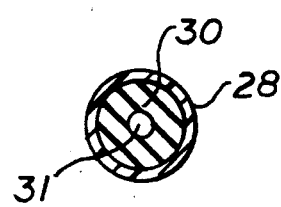
FIG. 5
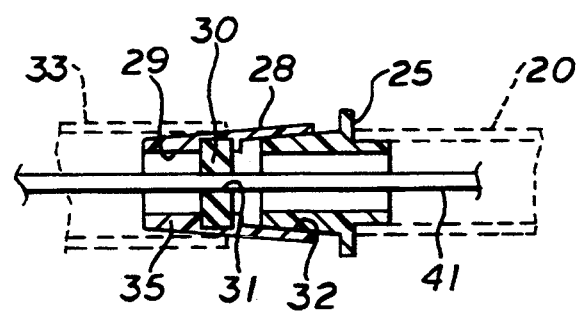
FIG. 4

ORAL FIBEROPTIC INTUBATING APPARATUS AND METHOD

BACKGROUND OF THE INVENTION

Field of the Invention

This invention relates generally to medical instruments and laryngoscopes used to intubate patients, and more particularly to a fiberoptic intubating apparatus having a removable handle and blade which removably carries an endotracheal tube and a flexible fiberoptic bronchoscope having its fiberoptic bundle inside the endotracheal tube.

Brief Description of the Prior Art

Endotracheal intubation is a medical procedure which concerns placement of a tube in the trachea of a patient to facilitate breathing or to permit the controlled introduction of gasses through the tube by an anesthesiologist or other medical personnel. Endotracheal intubation is normally carried out after induction of anesthesia or in emergencies, and is usually accomplished without great difficulty under direct vision with a laryngoscope by the anesthesiologist. The laryngoscope is an instrument used to examine the larynx (the uppermost end of the trachea narrowed by two surrounding vocal cords and located below the root of the tongue).

With direct laryngoscopy, the patient's neck is flexed, the head is extended and the mouth is opened wide. A laryngoscope having a rigid straight blade (commonly known as a Miller-type blade), or a rigid curved blade (commonly known as a Macintosh-type blade) is placed along the right side of the tongue, and the tongue and soft tissues of the mouth are retracted anteriorly and inferiorly to enable the larynx to be seen directly through the mouth in a straight line, instead of the normal anatomic curve around the tongue from the mouth to the larynx. The endotracheal tube is then placed directly into the trachea, along this direct line of vision.

Occasionally, however, the anesthesiologist is unable to visualize the larynx using the traditional direct laryngoscopy method in a patient who has no history or signs by physical examination of being a difficult intubation. For example, many patients have decreased mobility of the head and neck, protruding upper teeth, limited mouth opening, abnormally large or small mandibles, large tongues, tumors in the oropharynx or larynx, or trauma to the face and neck, all of which prevent direct visualization for intubation of the larynx and trachea. These types of patients are usually intubated while awake and through the nose blindly or via fiberoptic endoscopy so a wide open protected airway can be maintained by the patient until it is secured by the anesthesiologist. The fiberoptic endoscope is a tubular instrument which utilizes flexible fiberoptic bundles to transmit light and visual images during examination and intubation.

Bronchoscopes are sometimes used during endotracheal intubation. A bronchoscope is a tubular instrument usually with an optical system which is designed to pass through the trachea to allow visual inspection of the tracheobronchial tree. The bronchoscope is also sometimes designed to permit passage of an instrument than can be used to obtain tissue or remove a foreign body. A fiberoptic bronchoscope is a bronchoscope which utilizes flexible fiberoptic bundles to transmit light and visual images during examination. It also contains one longitudinal channel extending from the rearward end to the tip which can be used for suctioning or insufflation of oxygen, and a lever at the proximal end to maneuver the tip up and down during use.

There are several patents which disclose various instruments used for laryngoscopy and endotracheal intubation.

Frankel, U.S. Pat. No. 4,793,327 discloses a blind intubation device which consists of an airway opening device which is inserted into the patient's mouth and adjusted to a fixed position to hold the mouth open while an automatic intubation guide is inserted for guiding an endotracheal tube into the trachea. The airway opening device has an opening through which the guide is fed into the mouth. An endotracheal tube is also fed through the airway opening device and by means of an adapter or track on the guide, the endotracheal tube is inserted into the trachea, after which the guide is withdrawn and the airway opening device is retracted from its fixed position and removed from the mouth.

Fletcher, U.S. Pat. No. 4,329,983 discloses a guide device for endotracheal tubes which includes a flexible bar that is inserted into the endotracheal tube and has a flexible line which extends along the bar and is manipulated to flex the bar in bowed fashion against the endotracheal tube to urge the tube forwardly toward the trachea and away from the esophagus. It can be used along with direct laryngoscopy in difficult patients to help facilitate passage of the endotracheal tube through the larynx.

Phillips, U.S. Pat. No. 3,856,001 discloses a rigid laryngoscope blade having a straight portion and a curved portion with a longitudinal channel for passing an endotracheal tube. An electrical lamp is secured on one side of the blade at the forward end of the straight portion and aimed inwardly and downwardly and electrical wires extend from the lamp to the handle, which contains a power source.

Bullard, U.S. Pat. No. 4,086,919 discloses a rigid fiberoptic laryngoscope having a curved blade with a connection member at the proximal end for connection to a laryngoscope handle and an eyepiece that extends outwardly from the blade at the proximal end. Fiberoptic bundles extend along the longitudinal axis of the blade and terminate at the end of the blade. An endotracheal tube may be passed beneath the blade, alongside the fiberoptic bundle into the trachea.

Lowell, U.S. Pat. No. 4,306,547 discloses a rigid fiberoptic laryngoscope having a forwardly extending blade and a tube supporting channel. A viewing assembly and light source are each connected to fiberoptic bundles which extend longitudinally through the length of the top wall and terminate at the open end of the channel.

Wu, U.S. Pat. NO. 4,982,729 discloses a rigid fiberoptic laryngoscope having an integral handle and curved blade with fiberoptic bundles which extend longitudinally through the length of the blade and terminate at the end of the blade. A bivalve element is releasably attachable to the blade to form a passageway for threading an endotracheal tube through the distal end of the blade.

Augustine, U.S. Pat. No. 5,203,320 discloses a rigid tubular contoured fiberoptic tracheal intubation guide having a through bore for holding an endotracheal tube. Correct positioning of the device is detected by external palpation of the neck of the patient and tracheal intubation is confirmed with fiberoptic visualization.

MacAllister, U.S. Pat. No. 5,016,614 discloses an endotracheal intubation apparatus having a handle and mechanism for retaining an endotracheal tube on an elongated obturator element extending from the handle and releasing the endotracheal tube therefrom. The obturator element accommodates an endoscope therethrough to permit visualization at the end thereof.

Parker, U.S. Pat. No. 5,038,766 discloses a disposable, one-piece, contoured guide element having a channel therethrough which is releasably mounted at the end of a curved blade and handle. The device is used for blindly guiding and aiming orolaryngeal and oroesophogeal tubular members.

Blind techniques of endotracheal intubation are clearly the least advantageous, as stylets, obturators, or other guides can injure the patient, and there is no visual evidence that the endotracheal tube has correctly entered the trachea.

Direct laryngoscopy requires mouth opening and head and neck positioning that may be impossible or injurious to a patient with head or neck trauma. The larynx may never be able to be identified, or the endotracheal tube may not be able to be passed through it, even if it is identified. There is usually no means for oxygen delivery or suctioning during laryngoscopy.

Rigid fiberoptic laryngoscopy will aid in locating the larynx, but it is frequently difficult to guide the endotracheal tube into the trachea without rigid stylets or other guides, which may damage the soft tissues of the head and neck. Potential obstruction of the light source or field of view by the tube itself, secretions, blood, or soft tissues, and inability to confirm proper final tube position in the trachea are drawbacks that are still present.

Lastly, independent endoscope techniques, such as flexible fiberoptic bronchoscopy and the use of malleable fiberoptic stylets suffer from inability to effectively retract tissues away from the pathway of the instrument and the endotracheal tube over it, lack of a continuous field of view protected from blood, secretions, or soft tissues, and have the potential of stylet produced injury. It is also difficult or sometimes impossible to use these types of instruments with just one hand.

The present invention is distinguished over the prior art in general, and these patents in particular by an endotracheal intubating instrument that has an elongate curvilinear blade member releasably attachable to a handle and a central channel sized to removably receive and slidably engage an endotracheal tube therein, an elongate tubular housing removably connected at its forward end to the rearward end of the endotracheal tube which removably receives a fiberoptic scope having an eyepiece at a rearward end and a fiberoptic bundle extending forwardly within the endotracheal tube, and adjustable positioning means through which the forwardly extending fiberoptic bundle passes for adjustably positioning and maintaining the tip end of the fiberoptic bundle relative to the forward end of the endotracheal tube. The apparatus is placed in the mouth, the larynx is identified, and the endotracheal tube, housing, and fiberoptic scope are advanced as a unit into the trachea as the blade is removed. Then the fiberoptic scope and housing are withdrawn, leaving the endotracheal tube in the desired part of the trachea.

SUMMARY OF THE INVENTION

It is therefore an object of the present invention to provide a fiberoptic intubating apparatus and method which can be used to facilitate rapid, successful, and non-lethal oral endotracheal intubation of both awake and unconscious patients.

It is another object of the present invention to provide a fiberoptic intubating apparatus which can be used as a laryngoscope and to intubate the trachea either when the traditional and other laryngoscopes have failed, or when they cannot be used for various reasons.

Another object of this invention to provide a fiberoptic intubating apparatus and method which reduces the amount of pressure against the upper teeth, tongue and other soft tissues in the head and neck during laryngoscopy.

Another object of this invention is to provide a fiberoptic intubating apparatus and method which allows minimal mouth opening and minimal manipulation of the head and neck during intubation and laryngoscopy.

Another object of this invention is to provide a fiberoptic intubating apparatus which has a smooth blade that can both retract soft tissues, and hold and act as a conduit for an endotracheal tube into the trachea, without the need for stylets, forceps, or other rigid instruments that can injure the patient.

Another object of this invention is to provide a fiberoptic intubating apparatus which can be easily manipulated with one hand.

Another object of this invention is to provide a fiberoptic intubating apparatus for visualization and intubation of the trachea that has a flexible viewing portion and an external light source, both of which minimize risks of trauma or burn injury to the patient.

Another object of this invention is to provide a fiberoptic intubating apparatus and method which allows continuous manipulation of the endotracheal tube in an unchanging fixed position within the field of view, and subsequent confirmation of placement of the tube in the desired part of the trachea.

Another object of this invention is to provide a fiberoptic intubating apparatus that can be used for intubation with a continuous illuminated field of view during the whole process of endotracheal intubation, from beginning to end.

Another object of this invention is to provide a fiberoptic intubating apparatus that protects the illuminated field of view of from obstruction by soft tissues, secretions or blood throughout the whole process of endotracheal intubation.

A further object of this invention is to provide a fiberoptic intubating apparatus that allows both oxygen insufflation to the patient and suction to enhance visualization and help preclude lethal aspiration of vomitus during laryngoscopy and intubation.

A still further object of this invention is to provide a fiberoptic intubating apparatus which is simple in construction, economical to manufacture, and is rugged and reliable in use.

Other objects of the invention will become apparent from time to time throughout the specification and claims as hereinafter related.

The above noted objects and other objects of the invention are accomplished by an endotracheal intubating instrument that has an elongate curvilinear blade member releasably attachable to a handle and a central channel sized to removably receive and slidably engage an endotracheal tube therein, an elongate tubular housing removably connected at its forward end to the rearward end of the endotracheal tube which removably receives a fiberoptic scope having an eyepiece at a rearward end and a fiberoptic bundle extending forwardly within the endotracheal tube, and adjustable positioning means through which the forwardly extending fiberoptic bundle passes for adjustably positioning and maintaining the tip end of the fiberoptic bundle relative to the forward end of the endotracheal tube. The apparatus is placed in the mouth, the larynx is identified, and the endotracheal tube, housing, and fiberoptic scope are advanced as a unit into the trachea as the blade is removed. Then the fiberoptic scope and housing are withdrawn, leaving the endotracheal tube in the desired part of the trachea.

BRIEF DESCRIPTION OF THE DRAWINGS

FIG. 4 is a longitudinal cross section of the hollow tubular connector member of the apparatus.

FIG. 5 is a transverse cross section of the hollow tubular connector member of the apparatus showing the resilient washer element.

FIG. 6 is a side elevation of the tubular housing which is to be engaged via the connector member on the tubular extension at the rear of the endotracheal tube and carries a fiberoptic bronchoscope.

DESCRIPTION OF THE PREFERRED EMBODIMENT

Figure 1:
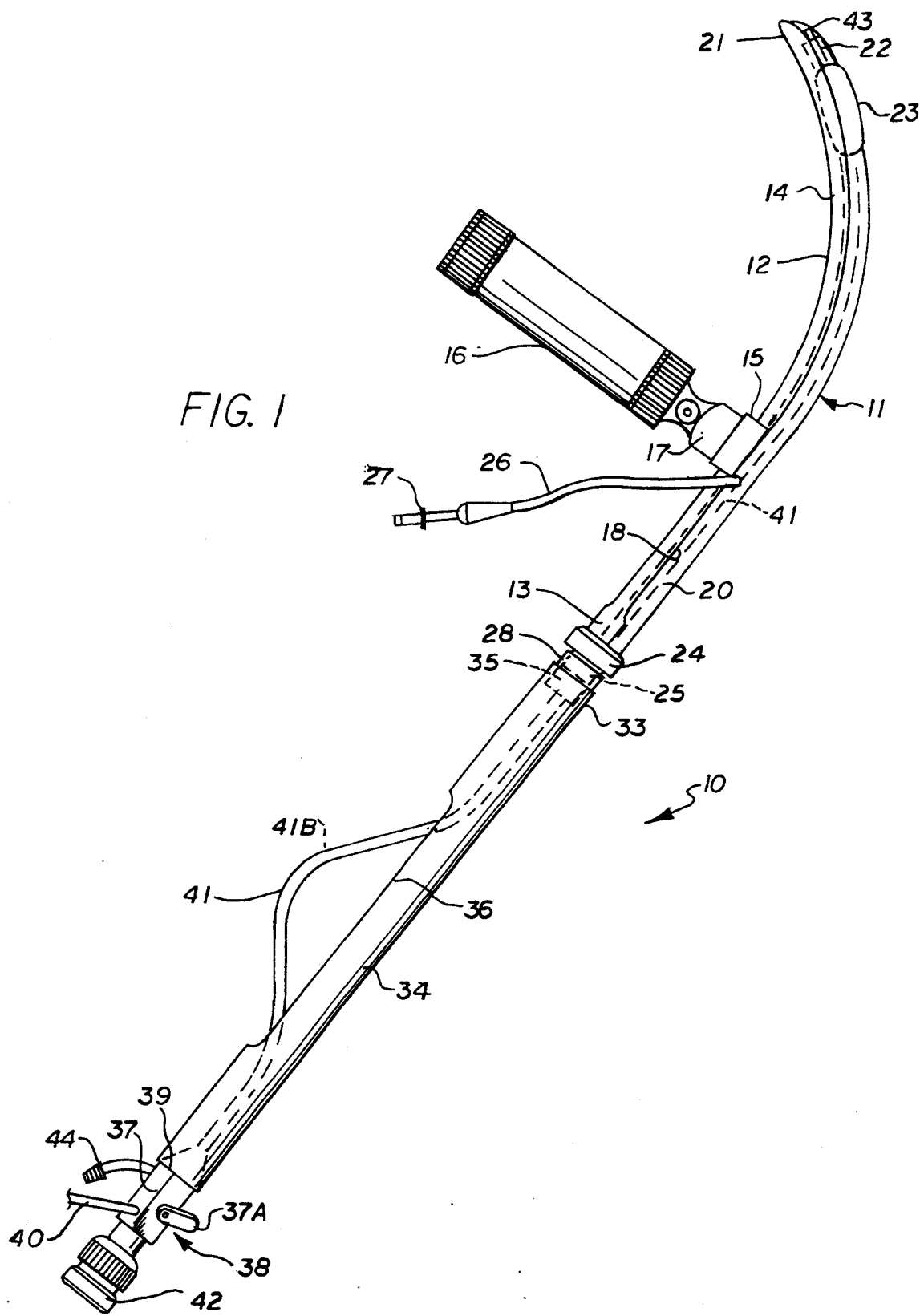
FIG. 1 is a side elevation of the assembled fiberoptic intubating apparatus in accordance with the present invention.
Figure 2:
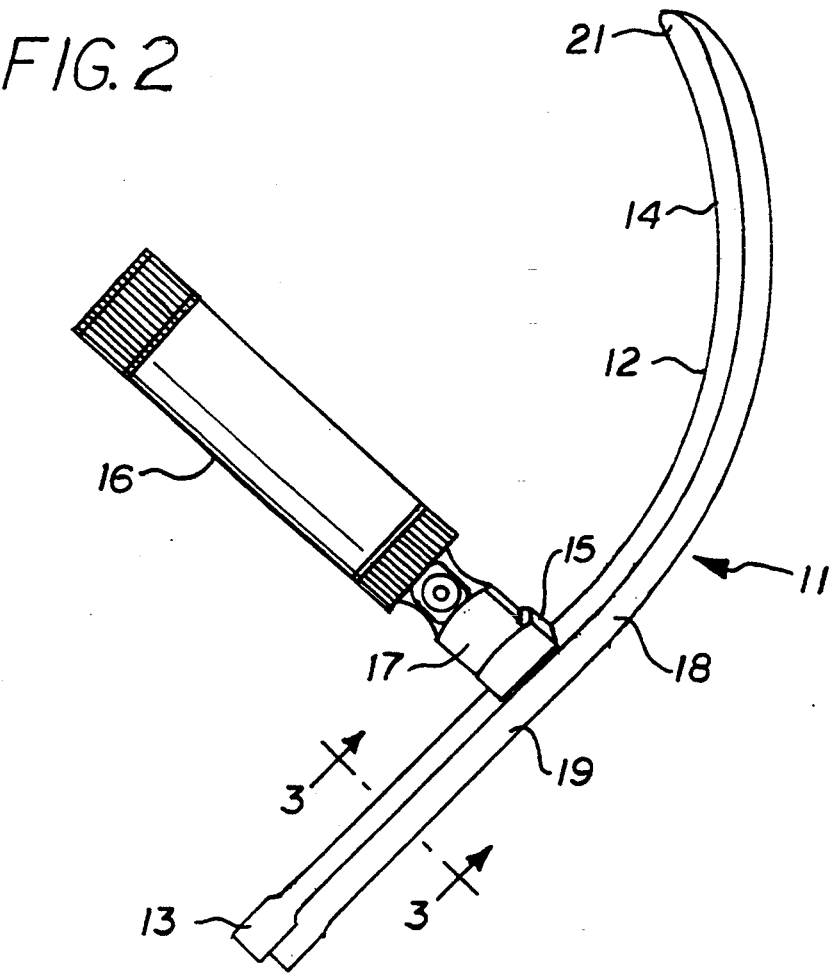
FIG. 2 is a side elevation of the handle and curved blade at the forward portion of the fiberoptic intubating apparatus.

Referring to the drawings by numerals of reference, there is shown in FIG. 1, a preferred fiberoptic intubating instrument 10 in accordance with the present invention. As seen in FIGS. 1 and 2, the forward or distal portion 11 of the device has a curved blade 12 formed of rigid material with a straight rearward or proximal portion 13 and an arcuate forward or distal portion 14. A flange element 15 is provided on the exterior of the blade 12 near the juncture of the straight and curved portions 13 and 14. A cylindrical handle 16 having a flange receptacle 17 at one end is removably engaged with the flange 15 on the blade 12 for manipulating the instrument with one hand.

Figure 3:
FIG. 3 is a transverse cross section of the curved blade member taken along line 3—3 of FIG. 2.

The blade 12 is generally C-shaped in transverse cross section (FIG. 3) with the opening 18 of the C-shape extending longitudinally along one side (right hand side as shown in the drawings) to define a central channel 19 which slidably and removably carries a flexible endotracheal tube 20. The interior diameter of the blade 12 and width of the opening 18 are sized relative to the exterior diameter of the flexible endotracheal tube 20 and partially surround the tube such that the flexible endotracheal tube can be pressed laterally through the opening 18, and once received in the blade 12 is held snugly within it during location of the larynx. The endotracheal tube 20 can then be slid along the longitudinal axis of the blade 12 and unclipped laterally from the blade (to the right) during advancement into the trachea, as described hereinafter, avoiding the need for stylets or forceps.

The forward or distal end of the curved portion 14 of the blade 12 is tapered to a flat spatulated tip 21 which serves as the leading edge and functions to lift the epiglottis up out of the field of vision (described hereinafter). The tip 21 has a smooth rounded contour. The longitudinal axis of the blade tip 21 and the longitudinal axis of the handle 16 are disposed at an angle of from about 30°–45° relative to one another so that as the blade 12 is passed into the mouth along the tongue, and the handle 16 is rotated upwardly about 30°–45° the blade tip 21 will pull the epiglottis up out of the way and become aligned with the larynx, keeping the rearward or proximal (outer) portion 13 of the blade parallel to the axis of the mouth. Since the arcuate shape and the direction of advancement of the blade 12 follow the normal anatomy of the mouth, the smooth rounded blade tip 21 can reach the larynx with minimal maneuvering of the head and neck, and minimal pressure on the teeth, tongue, and other tissues present.

Figure 2A:
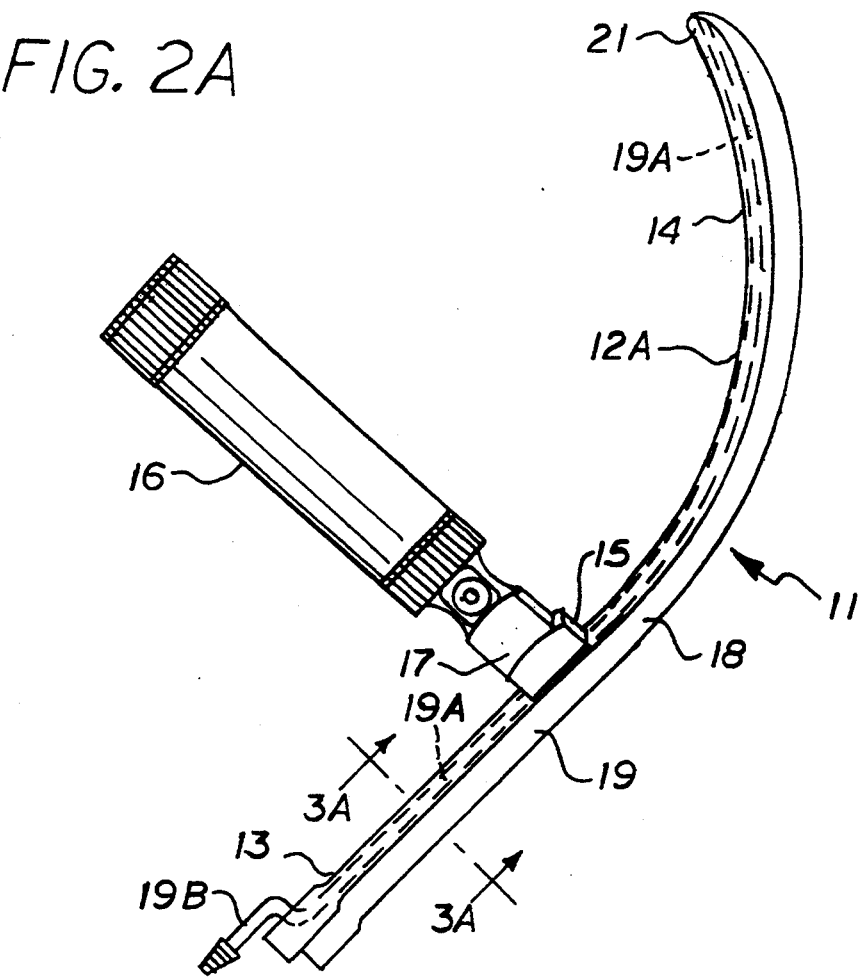
FIG. 2A is a side elevation of an alternate embodiment of the blade having an oxygen insufflation and suction feature.
Figure 3A:
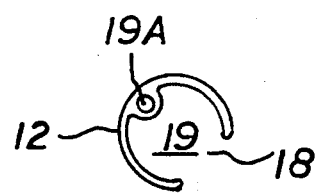
FIG. 3A is a transverse cross section of the alternate curved blade embodiment taken along line 3A—3A of FIG. 2A.

FIGS. 2A and 3A show an alternate embodiment of the blade 12A which has an oxygen insufflation and suction feature. The blade 12A has the same structural features described previously with reference to blade 12 which are given the same numerals of reference but will not be described in detail to avoid repetition. The blade 12A is generally C-shaped in transverse cross section (FIG. 3A) with the opening 18 of the C-shape extending longitudinally along one side (right hand side as shown in the drawings) to define a central channel 19 which slidably and removably carries a flexible endotracheal tube 20 as described previously. The side wall of the blade 12A opposite the opening 18 is provided with a longitudinal port 19A which extends along the length of the blade from the rearward end 13A and terminates at the tip 21 at the forward or distal end. The port 19A is connected to a fitting 19B which is adapted for connection to a source of vacuum and oxygen (not shown) to allow the operator to apply suction or insufflation at the tip of the blade 12A.

The flexible endotracheal tube 20 which is carried in the curved blade 12 or 12A is of conventional construction, and therefore, not shown in detail. The flexible endotracheal tube 20 contains a longitudinal lumen throughout its length to be used for ventilation or suction of the patient's trachea. It has an open rounded front end or tip 22 with an inflatable cuff 23 near the front end that surrounds the tube and is inflated after the tube is properly placed in the trachea. The rearward end of the endotracheal tube 20 receives an insert 20A having a radial flange portion 24 and a short tubular extension 25 which is of standard size to fit any manual or mechanical breathing circuit (conventional in the art, and therefore not shown). The inflatable cuff 23 at the forward end of the endotracheal tube 20 is connected by a conduit 26 to a fitting 27 for attachment to a conventional cuff inflation apparatus, such as an air filled syringe (not shown).

A hollow tubular connector member 28, as best seen in FIGS. 4 and 5, has a central bore 29 with a resilient disk or washer 30 mounted on the interior intermediate its ends. The resilient washer 30 has a central aperture 31. The forward end 32 of the tubular connector member 28 is dimensioned to be removably received and frictionally engaged on the tubular extension 25 at the rear of the endotracheal tube 20.

The forward end 33 of an elongate tubular housing 34 is removably received and frictionally engaged on the rearward end 35 of the tubular connector 28. The tubular housing 34 has a longitudinal slot 36 in its side wall which extends along its length and terminates a short distance from each end.

The neck portion 37 of a tubular fiberoptic scope instrument 38, such as a bronchoscope, is removably received and frictionally retained in the rearward or outer end 39 of the tubular housing 34. The fiberoptic scope instrument or bronchoscope 38 is of conventional construction, and therefore, not shown in detail. The fiberoptic scope instrument 38 is connected by a fiberoptic cable 40 to a light source (not shown) and has a forwardly extending elongate flexible fiberoptic bundle 41 which transmits light and visual images during examination. The fiberoptic scope instrument 38 has an eyepiece 42 at the outer end of the neck portion 37. Alternatively, the fiberoptic scope instrument 38 may also be connected to a display screen for displaying the image seen through the fiberoptic bundle 41. The conventional fiberoptic scope instrument 38 is also provided with a longitudinal insufflation an vacuum lumen 41A which extends along its length and terminates at the tip 43 at the forward or distal end of the fiberoptic bundle 41. The lumen 41A is connected via a fitting 44 to a source of vacuum or oxygen which allows the operator to apply suction or insufflation at the tip of the fiberoptic scope instrument 38. The fiberoptic scope instrument 38 is also provided with a longitudinal cable 41B connected to a control lever 37A pivotally connected at the rearward end 37 of the scope instrument for manipulating the tip end of the fiberoptic bundle up or down upon pivotal movement of the lever.

The width of the longitudinal slot 36 of the tubular housing 34 is preferably from 1½ to 2 times the diameter of the fiberoptic bundle 41. The fiberoptic bundle 41 extends forwardly through the tubular housing 34, the central aperture 31 of the resilient washer 30 in the connector member 28 and through the endotracheal tube 20 (FIG. 4.)

The central aperture 31 of the resilient washer 30 inside the tubular connector member 28 is slightly smaller in diameter than the exterior diameter of the fiberoptic bundle 41 so as to allow the fiberoptic bundle 41 to pass through it when minimal force is applied axially to the bundle, but will also frictionally hold the bundle snugly in place when the forward end or tip 43 of the fiberoptic bundle is properly positioned.

OPERATION

When assembled for use (FIG. 1), the fiberoptic scope instrument or bronchoscope 38 is fixed into place within the tubular housing 34, the fiberoptic bundle 41 is extended through the resilient washer 30 in the connector member 28, the connector member is installed in the forward end 33 of the tubular housing, and the tubular extension 25 of the endotracheal tube 20 is installed in the forward end 32 of the connector member. The tip 43 of the fiberoptic bundle 41 is positioned just rearward or proximal to the tip 22 of the endotracheal tube 20. The excess length, or midsection of the fiberoptic bundle 41 loops outwardly through the slot 36 in the side of the tubular housing 34 so that it can be manually manipulated to properly position the tip end 43 of the fiberoptic bundle.

The assembled fiberoptic scope instrument 38, tubular housing 34, and endotracheal tube 20, as a unit is then clipped snugly into the blade 12 or 12A so that the tip 22 of the endotracheal tube 20 rests just rearward or proximal to the tip 21 of the blade, and only the tubular extension 25 and flange 24 at the rearward or proximal end of the endotracheal tube 20 extends from the rearward or proximal end 13 of the blade 12 or 12A.

The field of view seen through the eyepiece 42 (or display screen) begins just rearward or proximal to the forward or distal end 22 of the endotracheal tube 20. The distal end 22 of the endotracheal tube 20 surrounding the fiberoptic bundle 41 and the tip 21 of the blade 12 or 12A provide protection of the visual field from obstruction by soft tissues, blood or secretions.

Figure 7:
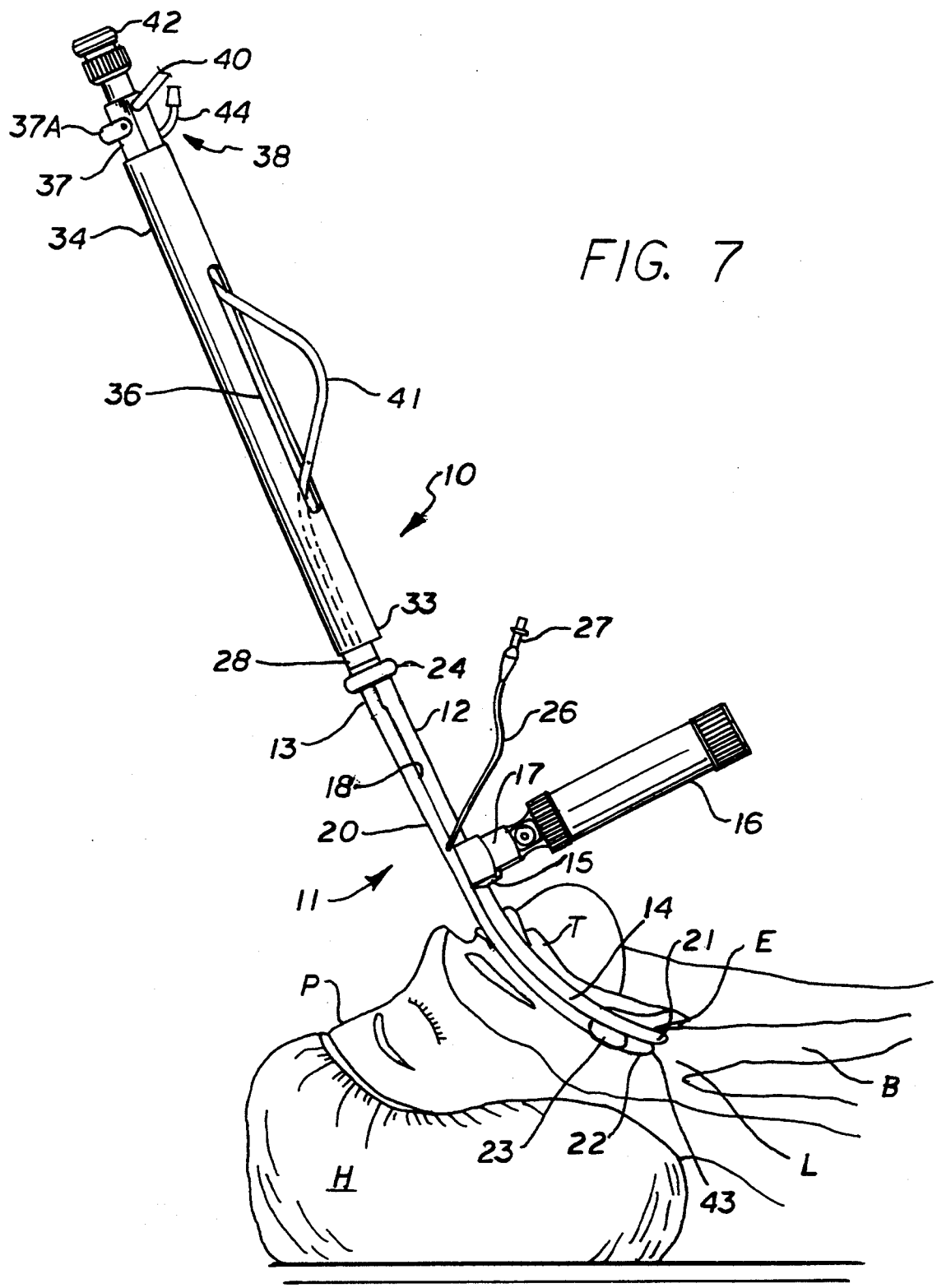
FIG. 7 is a side view in partial cross section showing the assembled fiberoptic intubating apparatus in the mouth of a patient.

The head H of the patient P may be kept in neutral position as the blade 12 or 12A at the forward end of the assembled instrument 10 is placed in the patient's mouth, behind and to the right of the tongue T (FIG. 7). The assembly is upwardly rotated as it is advanced into the mouth. As the blade 12 or 12A is passed into the mouth along the tongue, and the handle 16 is rotated upwardly about 30°-45° the blade tip 21 will pull the epiglottis E up out of the way and become aligned with the larynx L keeping the rearward or proximal portion 13 of the blade 12 or 12A parallel to the axis of the mouth. The operator can use the free right hand to open the mouth, manipulate the head, or whatever else is needed. Oxygen insufflation or suction can be provided during the procedure through the fiberoptic scope instrument or through the port 19A of the blade 12A.

Figure 8:
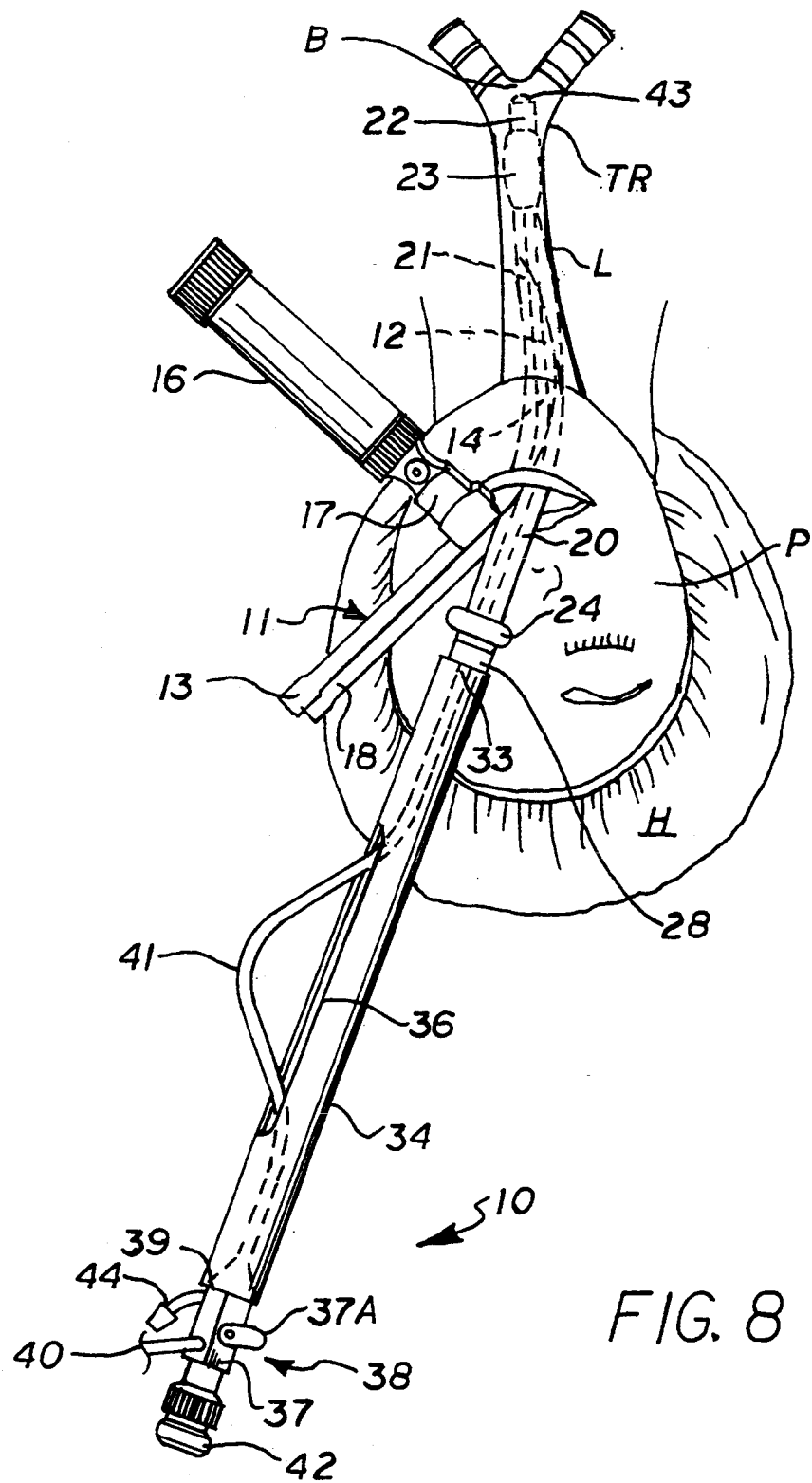
FIG. 8 is a top plan view of the fiberoptic intubating apparatus being advanced into the trachea as the blade and handle are withdrawn from the mouth of the patient.

After manipulation of the assembled instrument as needed, the assembled fiberoptic scope instrument 38, tubular housing 34, tubular connector member 28, and endotracheal tube 20 is threaded, as a single unit, straight into the trachea TR under continuous visualization through the eyepiece 42 as the handle 16 and blade 12 or 12A are disconnected from the endotracheal tube 20 and removed from the mouth (FIG. 8).

Advancement of the endotracheal tube with the forward portion of the fiberoptic bundle inside continues as a unit until the right and left bronchial openings B are identified. The fiberoptic scope instrument 38, the tubular housing 34, and tubular connector member 28 are then removed as a single unit from the mouth, leaving the tip 22 of the endotracheal tube 20 in the desired position of the trachea TR, a few centimeters above the bronchial openings B (FIG. 8).

The fiberoptic scope instrument 38, tubular housing 34, tubular connector 28 and endotracheal tube 20, can be rotated as a single unit during advancement to allow easier passage through the larynx L. Also, if necessary, the fiberoptic scope instrument 38 alone can be maneuvered into the trachea by advancement relative to the endotracheal tube and lever manipulation, followed by advancement of the endotracheal tube 20 along the forward portion of the fiberoptic bundle 41 into the trachea, after the blade 12 or 12A and handle 16 are removed from the mouth.

Because the tip 43 of the fiberoptic bundle 41 is inside the endotracheal tube, and also protected by the blade tip 21, the present intubating instrument provides a continuous unobstructed illuminated field of view. It allows continuous manipulation of the endotracheal tube in an unchanging fixed position within the field of view, and subsequent confirmation of placement of the tube in the desired part of the trachea, and it protects the illuminated field of view from soft tissues, secretions or blood throughout the whole process of endotracheal intubation.

While this invention has been described fully and completely with special emphasis upon a preferred embodiment, it should be understood that within the scope of the appended claims the invention may be practiced otherwise than as specifically described herein.

We claim:

1. A medical instrument for oral fiberoptic endotracheal intubation comprising in combination;
    an endotracheal tube having an interior and exterior diameter, a rearward end, and a forward tip end;
    an elongate curvilinear blade member having means thereon for removable attachment to a handle, said blade member having a generally C-shaped transverse cross section and having a straight rearward portion and an arcuate forward portion tapered smoothly inward along its length and terminating in a flat spatulated curved tip end, and said C-shaped cross section defining a central channel sized to removably receive and slidably engage said endotracheal tube therein;
    a fiberoptic scope having viewing means connected at a rearward end and an elongate thin flexible fiberoptic bundle which transmits light and visual images extending forwardly therefrom and terminating in a tip end and having midsection therebetween;
    an elongate tubular housing having a forward end and a rearward end configured to removably receive and engage said fiberoptic scope with a forward portion of said fiberoptic bundle of said fiberoptic scope received within said endotracheal tube; and
    removable connector means at said forward end of said tubular housing for removably connecting said housing to said rearward end of said endotracheal tube and having adjustable positioning means therein through which said forwardly extending fiberoptic bundle of said fiberoptic scope passes for adjustably positioning and maintaining said tip end of said fiberoptic bundle relative to said forward tip end of said endotracheal tube.

2. The medical instrument according to claim 1 in which
    said blade member is generally C-shaped in transverse cross section with the opening of the C-shape extending longitudinally along one side,
    the interior diameter of said blade and width of said opening are sized relative to said exterior diameter of said endotracheal tube to partially surround said endotracheal tube such that said endotracheal tube can be pressed laterally through said opening and slidably engaged with said blade member during location of the larynx of a patient while allowing said endotracheal tube to slide longitudinally relative to said blade member, such that
    said endotracheal tube can be slid along the longitudinal axis of said blade member and disconnected therefrom by pulling it laterally outward therefrom during advancement into the trachea of the patient.

3. The medical instrument according to claim 1 in which
    said adjustable positioning means in said removable connector means a resilient member having a central aperture through which said forwardly extending fiberoptic bundle of said fiberoptic scope passes and is frictionally and slidably engaged therewith so as to allow said fiberoptic bundle to slide relative thereto when minimal axial force is applied to said fiberoptic bundle for adjustably positioning and maintaining said tip end of said fiberoptic bundle relative to said forward tip end of said endotracheal tube.

4. The medical instrument according to claim 1 in which
    said elongate tubular housing has a longitudinal slot in its side wall through which a portion of said midsection of said fiberoptic bundle may be extended so as to allow manual manipulation of said fiberoptic bundle to selectively position said tip end of said fiberoptic bundle relative to said forward tip end of said endotracheal tube.

5. The medical instrument according to claim 1 in which
    said removable connector means comprises a short tubular connector having a forward end adapted for removable connection to said rearward end of said endotracheal tube and a rearward end for removable connection to said elongate tubular housing.

6. The medical instrument according to claim 1 in which
    said forward tip end of said endotracheal tube has an open rounded front tip end with an inflatable cuff near said front tip end that surrounds said endotracheal tube and a conduit connected with said inflatable cuff which has a fitting at an outer end for attachment to a cuff inflation apparatus.

7. The medical instrument according to claim 1 in which
    said blade member has a longitudinal port which extends along the length of said blade from said rearward portion and terminates at said tip end of said blade and is adapted at said rearward end for connection to a source of oxygen or vacuum for applying insufflation or suction at said tip end of said blade.

8. The medical instrument according to claim 1 in which
    said forward portion of said fiberoptic bundle passes through said adjustable positioning means and is received within said interior diameter of said endotracheal tube, and
    said fiberoptic scope has a neck portion between said viewing means and said fiberoptic bundle removably received and engaged on said rearward end of said elongate tubular housing.

9. The medical instrument according to claim 8 in which
    said fiberoptic scope has a longitudinal insufflation and vacuum lumen which extends along its length and terminates at said tip end of said fiberoptic bundle, and
    said insufflation and vacuum lumen adapted for connection to a source of oxygen or vacuum for applying insufflation or suction at said tip end of said fiberoptic bundle.

10. The medical instrument according to claim 8 in which
    said fiberoptic scope has a longitudinal cable which extends along its length and is connected to said tip end of said fiberoptic bundle, and a control lever pivotally connected to said rearward end of said fiberoptic scope and to said cable for manipulating said tip end of said fiberoptic bundle up or down upon pivotal movement of said lever.

11. In a medical instrument for oral fiberoptic endotracheal intubation which has an endotracheal tube with a rearward end and a forward tip end and a fiberoptic scope with a viewing means at a rearward end and an elongate thin flexible fiberoptic bundle that transmits light and visual images extending forwardly therefrom and terminating in a tip end and having a midsection therebetween, an adapter comprising;

an elongate rigid tubular adapter having connector means at a forward end for removable connection to said rearward end of said endotracheal tube, and a rearward end configured to removably receive and engage said viewing means of said fiberoptic scope with said forwardly extending elongate thin flexible fiberoptic bundle received within said endotracheal tube; and adjustable positioning means connected with said adapter through which said forwardly extending fiberoptic bundle of said fiberoptic scope passes for adjustably positioning and maintaining said tip end of said fiberoptic bundle relative to said forward tip end of said endotracheal tube.

12. The adapter according to claim 11 in which
said tubular adapter has a longitudinal slot in its side wall through which a portion of said midsection of said fiberoptic bundle may be extended so as to allow manual manipulation of said fiberoptic bundle to selectively position said tip end of said fiberoptic bundle relative to said forward tip end of said endotracheal tube.

13. The adapter according to claim 11 in which
said connector means at said forward end of said tubular adapter comprises a short tubular connector having a forward end adapted for removable connection to said rearward end of said endotracheal tube and a rearward end for removable connection to said tubular adapter forward end.

14. A medical instrument for use in oral fiberoptic endotracheal intubation to facilitate insertion of both an endotracheal tube and a fiberoptic scope, the instrument comprising:

an elongate curvilinear blade member having means thereon for removable attachment to a handle, said blade member having a generally C-shaped transverse cross section and having a straight rearward portion and an arcuate forward portion tapered smoothly inward along its length and terminating in a flat spatulated curved tip end, and said C-shaped cross section defining a central channel sized to removably receive and slidably engage an endotracheal tube of the type having an interior and exterior diameter, a rearward end, and a forward tip end;

an elongate tubular housing having a forward end and a rearward end configured to removably receive and engage a fiberoptic scope of the type having a viewing means at a rearward end, an elongate thin flexible fiberoptic bundle that transmits light and visual images extending forwardly therefrom and terminating in a tip end, and a midsection therebetween, a forward portion of the fiberoptic bundle of the fiberoptic scope being carried within the interior diameter of the endotracheal tube; and removable connector means at said forward end of said tubular housing for removably connecting said housing to the rearward end of the endotracheal tube received in said blade member channel and having adjustable positioning means therein to engage a portion of the forwardly extending fiberoptic bundle carried within the interior diameter of the endotracheal tube for adjustably positioning and maintaining the tip end of the fiberoptic bundle relative to the forward tip end of the endotracheal tube.

15. A method for introducing an endotracheal tube into a patient's trachea comprising:

providing a tubular elongate curvilinear blade contoured to be received at the laryngeal opening of the patient and having a longitudinal channel open at one side and handle means thereon for manipulating said blade with one hand;

installing an endotracheal tube in said blade channel for sliding movement relative thereto;

installing a fiberoptic scope instrument at a rearward end of the endotracheal tube, the fiberoptic scope having viewing means connected at a rearward end and a forwardly extending elongate thin flexible fiberoptic bundle terminating in a tip end which transmits light and visual images, a forward portion of the fiberoptic bundle being received within the center of the endotracheal tube and a midsection portion of the fiberoptic bundle extending outwardly from the endotracheal tube;

adjustably positioning and maintaining the tip end of the fiberoptic bundle relative to a forward tip end of the endotracheal tube by manual manipulation of the outwardly extending midsection portion of the fiberoptic bundle;

inserting the assembled blade and endotracheal tube with the forward portion of the fiberoptic bundle inside it into the patient's mouth along the tongue, and after the blade and endotracheal tube with the forward portion of the fiberoptic bundle inside is passed deep into the mouth along the tongue, raising the blade upwardly such that the tip of the blade will pull the epiglottis up out of the way and become aligned with the larynx; and under continuous visualization through the viewing means, advancing and rotating the endotracheal tube with the forward portion of the fiberoptic bundle inside forward relative to the blade to move the tip end of the endotracheal tube and the tip end of the fiberoptic bundle as a unit through the larynx of the patient as required until the right and left bronchial openings are identified, and while advancing the endotracheal tube and fiberoptic bundle, disconnecting the blade from the endotracheal tube and removing the blade from the patient's mouth; and thereafter disconnecting and removing the fiberoptic scope instrument from the endotracheal tube and withdrawing the fiberoptic bundle from within the endotracheal tube leaving the tip end of the endotracheal tube in the desired position of the trachea above the bronchial openings.

16. A method for introducing an endotracheal tube into a patient's trachea comprising:

providing a tubular elongate curvilinear blade contoured to be received at the laryngeal opening of the patient and having a longitudinal channel open at one side and handle means thereon for manipulating said blade with one hand;

installing an endotracheal tube in said blade channel for sliding movement relative thereto;

installing a fiberoptic scope instrument at a rearward end of the endotracheal tube, the fiberoptic scope having viewing means connected at a rearward end and a forwardly extending elongate thin flexible fiberoptic bundle terminating in a tip end which transmits light and visual images, a forward portion of the fiberoptic bundle being received within the center of the endotracheal tube and a midsection portion of the fiberoptic bundle extending outwardly from the endotracheal tube;

adjustably positioning and maintaining the tip end of the fiberoptic bundle relative to a forward tip end of the endotracheal tube by manual manipulation of the outwardly extending midsection portion of the fiberoptic bundle;

inserting the assembled blade and endotracheal tube with the forward portion of the fiberoptic bundle inside it into the patient's mouth along the tongue, and after the blade and endotracheal tube with the forward portion of the fiberoptic bundle inside is passed deep into the mouth along the tongue, raising the blade upwardly such that the tip of the blade will pull the epiglottis up out of the way and become aligned with the larynx; and under continuous visualization through the viewing means, advancing only the forward portion of the fiberoptic bundle forward relative to the endotracheal tube and the blade to move the tip end of the fiberoptic bundle through the larynx of the patient as required until the right and left bronchial openings are identified;

disconnecting the endotracheal tube from the blade and removing the blade from the patient's mouth and then advancing the endotracheal tube forward along the forward portion of the fiberoptic bundle; and thereafter disconnecting and removing the fiberoptic scope instrument from the endotracheal tube and withdrawing the fiberoptic bundle from within the endotracheal tube leaving the tip end of the endotracheal tube in the desired position of the trachea above the bronchial openings.

* * * * *